(12) United States Patent
Sekiwa et al.

(10) Patent No.: US 7,449,097 B2
(45) Date of Patent: Nov. 11, 2008

(54) ELECTROPHORETIC MOBILITY MEASURING APPARATUS

(75) Inventors: Mitsunao Sekiwa, Osaka (JP); Kazunori Tsutsui, Osaka (JP); Katsuhiro Morisawa, Kyoto (JP); Takashi Fujimoto, Kyoto (JP); Atsushi Toyoshima, Osaka (JP)

(73) Assignee: Otsuka Electronics Co., Ltd., Osaka (JP)

( * ) Notice: Subject to any disclaimer, the term of this patent is extended or adjusted under 35 U.S.C. 154(b) by 736 days.

(21) Appl. No.: 10/784,278

(22) Filed: Feb. 24, 2004

(65) Prior Publication Data

US 2004/0251134 A1    Dec. 16, 2004

(30) Foreign Application Priority Data

Feb. 25, 2003  (JP)  ............................. 2003-047824
Mar. 26, 2003  (JP)  ............................. 2003-085678

(51) Int. Cl.
  *G01N 27/453*  (2006.01)
(52) U.S. Cl. .................. 204/603; 204/452; 356/344
(58) Field of Classification Search ................. 204/603, 204/612, 452, 461; 356/344; 345/107; 359/296
See application file for complete search history.

(56) References Cited

U.S. PATENT DOCUMENTS

| | | | | |
|---|---|---|---|---|
| 3,708,402 A | * | 1/1973 | Bean ........................... | 204/645 |
| 3,766,048 A | | 10/1973 | Flygare et al. ............... | 204/299 |
| 3,866,055 A | * | 2/1975 | Pike ............................ | 250/564 |
| 4,025,200 A | * | 5/1977 | Zeineh ........................ | 356/432 |
| 4,059,067 A | | 11/1977 | Lardon et al. .................. | 118/7 |
| 4,097,153 A | * | 6/1978 | DeRemigis ................. | 204/549 |
| 4,101,220 A | | 7/1978 | Bean et al. .................. | 356/105 |
| 4,123,841 A | * | 11/1978 | Yano et al. .................... | 445/24 |
| 5,069,769 A | * | 12/1991 | Fujimiya et al. ............ | 204/461 |

(Continued)

FOREIGN PATENT DOCUMENTS

GB    2 368 904 A    5/2002

(Continued)

OTHER PUBLICATIONS

Tsutsui; "Interfacial Electrokinetic Phenomena of Polymer and Determination of Electrophoretic Mobility"; High Polymers, vol. 51, pp. 500-503, (2002).

*Primary Examiner*—Kaj K Olsen
(74) *Attorney, Agent, or Firm*—Finnegan, Henderson, Farabow, Garrett & Dunner, L.L.P.

(57) ABSTRACT

The present invention provides an electrophoretic mobility measuring apparatus capable of conducting measurement with high sensitivity with optical attenuation reduced by incidence of light through the electrode face. This apparatus comprises a transparent electrode 63 forming a part of a cell wall of a cell 6 capable of confining a sample, and the other electrode 62 opposite to the transparent electrode 63. A voltage is applied across these electrodes 62, 63, and light is incident upon the inside of the cell 6 through the transparent electrode 63. The scattering light which scatters from a sample S at a predetermined angle θ with respect to the incident angle, is received through the transparent electrode 63. The Doppler displacement is then measured based on the difference in frequency between the incident light and the outgoing light. The direction of the scattering vector which is the vector difference between incident and outgoing vectors, is substantially identical with that of the normal line h of the transparent electrode face.

23 Claims, 9 Drawing Sheets

U.S. PATENT DOCUMENTS

| | | | |
|---|---|---|---|
| 5,325,220 A * | 6/1994 | Saxe | 349/147 |
| 5,575,936 A * | 11/1996 | Goldfarb | 219/121.68 |
| 5,587,532 A * | 12/1996 | Rose | 73/579 |
| 2002/0040851 A1 * | 4/2002 | McNeil-Watson et al. | 204/549 |

FOREIGN PATENT DOCUMENTS

| | | |
|---|---|---|
| JP | 55-16253 | 2/1980 |
| JP | 55-113974 | 9/1980 |

* cited by examiner

Prior Art

ELECTROPHORETIC MOBILITY MEASURING APPARATUS

The disclosure of Japanese Patent Application No. 2003-47824, filed on Feb. 25, 2003, and Japanese Patent Application No. 2003-85678, filed on Mar. 26, 2003, is incorporated herein by reference.

FIELD OF THE INVENTION

The present invention relates to an electrophoretic mobility measuring apparatus capable of measuring the electrophoretic speed of particles in a solution.

DESCRIPTION OF RELATED ART

Polymers or their aggregates, i.e., colloid particles are electrically charged in a water solution by adsorption of dissociation groups or ions. The potential formed by such charging is called a zeta (ζ) potential. To measure the charge amount of particles, it has been practiced to apply an electric field to the particles for measuring the moving speed (electrophoretic mobility) thereof.

FIG. 13 is a schematic section view of a conventional electrophoretic mobility measuring apparatus. The electrophoretic mobility measuring apparatus has a rectangular parallelepiped or cylindrical cell 101 in which a sample (for example, a water solution containing polymers) S is confined. The cell 101 is provided at both ends thereof with electrodes 102, 103 made of platinum or the like. The cell 101 is also provided at each lateral side thereof with a transparent quartz glass. While a direct current voltage is applied across the electrodes 102, 103, a laser light is incident upon one lateral side 104 substantially vertically. Then, the outgoing light scattered at a predetermined angle (scattering angle) θ is received, and the difference in frequency (interference phenomenon) between the incident light and the outgoing light, is measured, thus calculating the moving speed of the particles in the sample S.

According to the arrangement in FIG. 13, the incident light enters the lateral side 104 vertically, and the scattering light outgoes obliquely. Accordingly, the direction of scattering vector q to be discussed later, is inclined by a scattering angle θ/2 with respect to the particle velocity direction (horizontal direction with respect to the drawing plane). To obtain the particle moving speed, it is therefore required to multiply the net scattering vector q by cos (θ/2) (See "Interfacial Electrokinetic Phenomena of Polymer and Determination of Electrophoretic Mobility" written by Kazunori TSUTSUI in HIGH POLYMERS, JAPAN, Volume 51, July Issue, P500-P503 (2002)).

The cell inside is filled with a measuring sample. The cell inside is generally optically arranged such that the incident light path and the detection light path intersect each other in the vicinity of the cell center, thus measuring the velocity of the particles present in the vicinity of the cell center. Accordingly, measurement has conventionally been made only of a very dilute solution in which the incident light is not attenuated even in the cell center portion. In other words, for a concentrated sample which causes the incident light to be greatly attenuated, the measuring precision has remarkably been deteriorated or the measurement itself could not be made.

To reduce the optical attenuation to enable the measurement to be made in a wider range of concentration, it is effective to measure the scattering light which is returned in the direction opposite to the direction of the incident light. In the arrangement, however, the scattering vector (See FIG. 11) serving as the vector to be observed is substantially at right angles to the electric field direction. This makes it difficult to measure the velocity of the particles which move in the electric field direction.

SUMMARY OF THE INVENTION

In view of the foregoing, it is an object of the present invention to provide an electrophoretic mobility measuring apparatus capable of conducting measurement with high sensitivity with optical attenuation reduced by incidence of light through the electrode face.

The present invention provides an electrophoretic mobility measuring apparatus comprising: a cell capable of confining a sample; a transparent electrode forming a part of a cell wall; the other electrode opposite to the transparent electrode; voltage applying means for applying a voltage across both electrodes; a light incident unit for entering light into the cell through the transparent electrode; a light receiving unit for receiving, through the transparent electrode, the outgoing light which scatters from the sample in the cell at a predetermined angle θ with respect to the incident angle; and a measuring unit for measuring the Doppler displacement based on the difference in frequency between the incident light and the outgoing light, the direction of scattering vector which is the vector difference between incident and outgoing vectors, being substantially identical with that of the normal line of the transparent electrode face.

According to the arrangement above-mentioned, when a voltage is applied across the transparent electrode and the other electrode to cause light to enter inside of the cell through the transparent electrode, there can be received the outgoing light which scatters from the sample at a predetermined angle θ with respect to the incident angle.

A unit vector in the propagation direction of the incident light is expressed by ki, and a unit vector in the propagation direction of the outgoing light is expressed by ks. FIG. 11 is a view illustrating the relationship between the incident vector ki and the outgoing vector ks. In FIG. 11, the scattering angle formed by the incident vector ki and the outgoing vector ks is expressed by θ. Vector q which is the difference between the incident vector ki and the outgoing vector ks, is called scattering vector:

$$q = ki - ks$$

According to the arrangement of the present invention, the direction of the scattering vector q is identical with that of the normal line of the transparent electrode. The Doppler displacement which can be measured by "the measuring unit for measuring the Doppler displacement based on the difference in frequency between the incident light and the outgoing light", is the displacement in the direction of the scattering vector q. Accordingly, the measuring unit can measure the velocity of the particles in the direction of the normal line of the transparent electrode. Since the direction of the normal line of the transparent electrode is the direction of the electric field, the direction of the scattering vector is substantially identical with that of the electric field. As a result, there can be measured the velocity of particles, along the direction of the electric field, located in a position which is not so inwardly remote from the electrode face.

When the cell-side face of the transparent electrode is coated with platinum or a platinum alloy, the platinum film or the platinum alloy film serves as a protective film for protecting the transparent electrode from the solution.

As a specific shape of the cell, the cell inside may be a rectangular parallelepiped or cylindrical casing-shape body, and the cell may be provided at both end faces thereof with the electrodes, one of which is the transparent electrode.

According to the arrangement above-mentioned, the scattering light measuring point is preferably located between the centerline of the casing-shape body, and the inner wall of a lateral face thereof. Referring to FIG. 1, the electrophoretic mobility of particles in the cell is expressed by an arrow D. In the vicinity of the transparent electrode 63 forming an end face of the casing-shape body, there is produced a return flow A1 of an electroosmotic flow A toward the center from the circumference. In FIG. 1, "B" designates, out of the zone in which the return flow A1 is generated, the region in which the direction of the return flow A1 is substantially parallel to the face of the transparent electrode 63 and in which the component of the normal line is small. When light is incident upon the region B in which the direction of the return flow A1 is substantially parallel to the face of the transparent electrode, the speed D of the particles in the sample along the normal line direction or the electric field direction, can be measured without any interruption by the electroosmotic flow in the normal line direction.

It is preferably arranged such that the transparent electrode is formed on a transparent substrate, that the light incident unit is arranged to enter light through one lateral face of the transparent substrate, and that the light receiving unit is arranged to receive the light which outgoes through the other lateral face of the transparent substrate. According to the arrangement above-mentioned, light is incident through the lateral face of the transparent electrode. Therefore, the light can be incident at a smaller angle as compared with the arrangement in which light is incident through the bottom of the transparent electrode. This enables a scattering measurement at a small angle to be conducted. In the electrophoretic mobility measurement, there are measured both the amount of scattering light frequency shift (Doppler shift) in proportion to the electrophoretic mobility, and the frequency spread due to particle diffusion. However, when the scattering angle is increased, the frequency spread due to diffusion is increased to lower the measuring resolution. In this connection, when provision is made such that the light is incident through one lateral face of the transparent electrode, this enables a scattering measurement at a small angle to be conducted, thus improving the measuring precision.

When the cell is arranged to be movable in the direction of the normal line of the transparent electrode face, and in the direction at right angles to this normal line direction, the scattering light measuring point (scattering volume portion) can be set to the best-suited position in the cell which is less subject to the influence of the electroosmotic flow. Further, when the scattering volume portion overlaps the solution-contact face of the transparent electrode, scattering light from the solution-contact face is received and serves as stray light, resulting in failure of accurate measurement. The movable arrangement of the cell eliminates such an inconvenient configuration or layout.

When the light incident unit or the light receiving unit uses a cylindrical lens for focusing the light on the scattering volume portion, the image distortion can be corrected to make the scattering volume portion smaller to avoid the influence of multiple scattering and/or scattering from the solution-contact face of the transparent electrode.

The present invention provides an electrophoretic mobility measuring apparatus comprising: a cell capable of confining a sample; an opaque electrode forming a part of a cell wall; the other electrode opposite to the opaque electrode; voltage applying means for applying a voltage across both electrodes; a light incident unit for entering light into the cell through the opaque electrode; a light receiving unit for receiving the outgoing light which scatters from the sample in the cell at a predetermined angle θ with respect to the incident angle; and a measuring unit for measuring a Doppler displacement based on the difference in frequency between the incident light and the outgoing light, the direction of scattering vector which is the vector difference between incident and outgoing vectors, is substantially identical with that of the normal line of the opaque electrode face, and the opaque electrode having (i) a transparent incident window upon which incident light is incident, and (ii) a transparent outgoing window through which outgoing light outgoes.

According to the arrangement above-mentioned, the electrode is not required to be transparent in its entirety as far as it has the incident window and the outgoing window. Incident light is incident upon the inside of the cell through the incident window, and scattering light outgoes from the scattering volume portion through the outgoing window. This eliminates the need of providing a protective film, thus simplifying the production step.

In this arrangement, too, the direction of the scattering vector is preferably substantially identical with that of the electric field.

The cell-side face of the opaque electrode may be coated with platinum or a platinum alloy.

It is preferably arranged such that the opaque electrode is formed on a transparent substrate, that the light incident unit is arranged to enter light through one lateral face of the transparent substrate, and that the light receiving unit is arranged to receive light which outgoes through the other lateral face of the transparent substrate.

Preferably, there is disposed cell driving means for moving the cell in the direction of the normal line of the opaque electrode face, and in the direction at right angles to this normal line direction.

Preferably, the light incident unit or the light receiving unit uses a cylindrical lens for focusing the light on the scattering volume portion.

According to the present invention having the arrangement above-mentioned, light is incident upon the inside of the cell through the transparent electrode, and the outgoing light which scatters from the sample at a predetermined angle θ with respect to the incident angle, is received through the transparent electrode. Further, the direction of the scattering vector which is the difference between the incident vector of the incident light and the outgoing vector of the scattering light, is set substantially identical with the direction of the normal line of the transparent electrode face. It is therefore possible to measure the velocity of the particles, along the direction of the normal line of the transparent electrode or the direction of the electric field, located in the vicinity of the transparent electrode face which is not so inwardly remote from the transparent electrode face in the cell. This enables measurement of particle moving speed with excellent sensitivity with optical attenuation reduced. Further, an opaque electrode having an incident window and an outgoing window may be used instead of the transparent electrode.

DESCRIPTION OF THE PREFERRED EMBODIMENTS

The following description will discuss embodiments of the present invention with reference to attached drawings.

Figure 3:
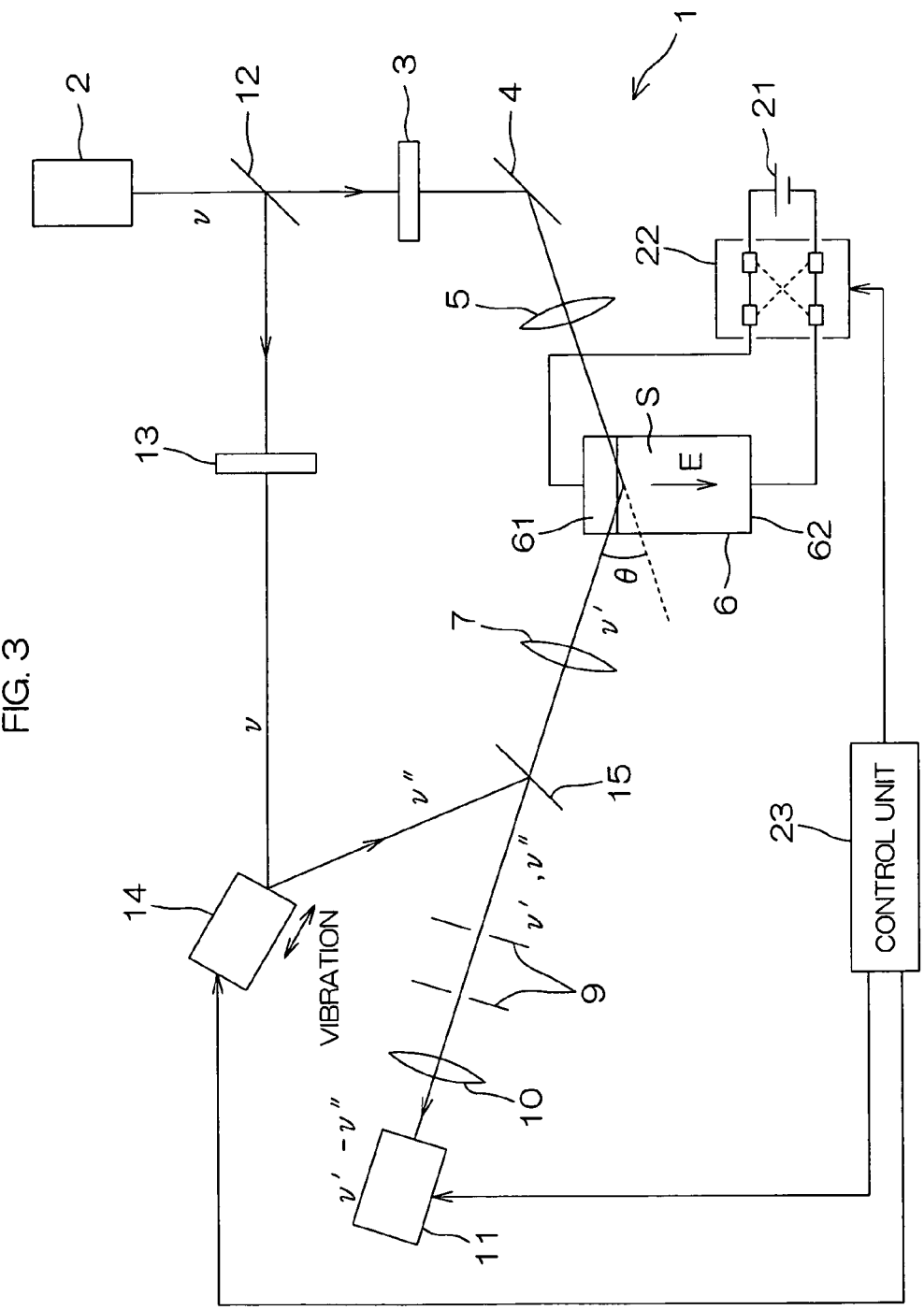
FIG. 3 is a general light path diagram of an electrophoretic mobility measuring apparatus 1 of the present invention.

FIG. 3 is a general optical path diagram of an electrophoretic mobility measuring apparatus 1. This electrophoretic mobility measuring apparatus 1 comprises an optical system comprising: a laser oscillator 2; a neutral density filter (ND filter) 3 for adjusting the amount of laser light emitted from the laser oscillator 2; a mirror 4 for reflecting the laser light; a lens 5 for causing the light to be incident upon a cell 6; the cell 6 which confines a sample S; a lens 7 for receiving the outgoing light which scatters from the sample S at a predetermined angle θ with respect to the incident angle; pinholes 9 and a lens 10 on the light receiving path; and a light receiving unit 11 formed by a photoelectron multiplier or a CCD element. Further, the apparatus 1 comprises a reference optical system comprising: a half mirror 12 for branching a part of the laser light emitted from the laser oscillator 2; an ND filter 13; a modulator 14 for vibrating a reflector plate in one direction to modulate the wavelength of the reflected light, thus forming a reference light; and a half mirror 15 for mixing the reference light from the modulator with the outgoing light above-mentioned.

No restrictions are imposed to the wavelength of the laser light. For example, there is used a red visible light of which wavelength is 633 nm. The frequency of the laser light is expressed by ν, the frequency of the scattering light is expressed by ν', and the frequency of the reference light is expressed by ν".

A direct-current voltage (for example, tens of volts) is applied to an electrode of the cell 6 from a direct current power source 21. When the direction of the electric field E remains in one direction, the electrophoretic direction of the particles in the solution is always the same direction, causing the particles to be biased to one side of the cell 6. Accordingly, there is disposed a changeover switch 22 for switching the direction of the electric field E per a predetermined period of time (for example, one second).

Disposed is a computer control unit 23 for controlling the switching operation of the changeover switch 22, and the operation of the modulator 14 and the light receiving unit 11.

Figure 4:
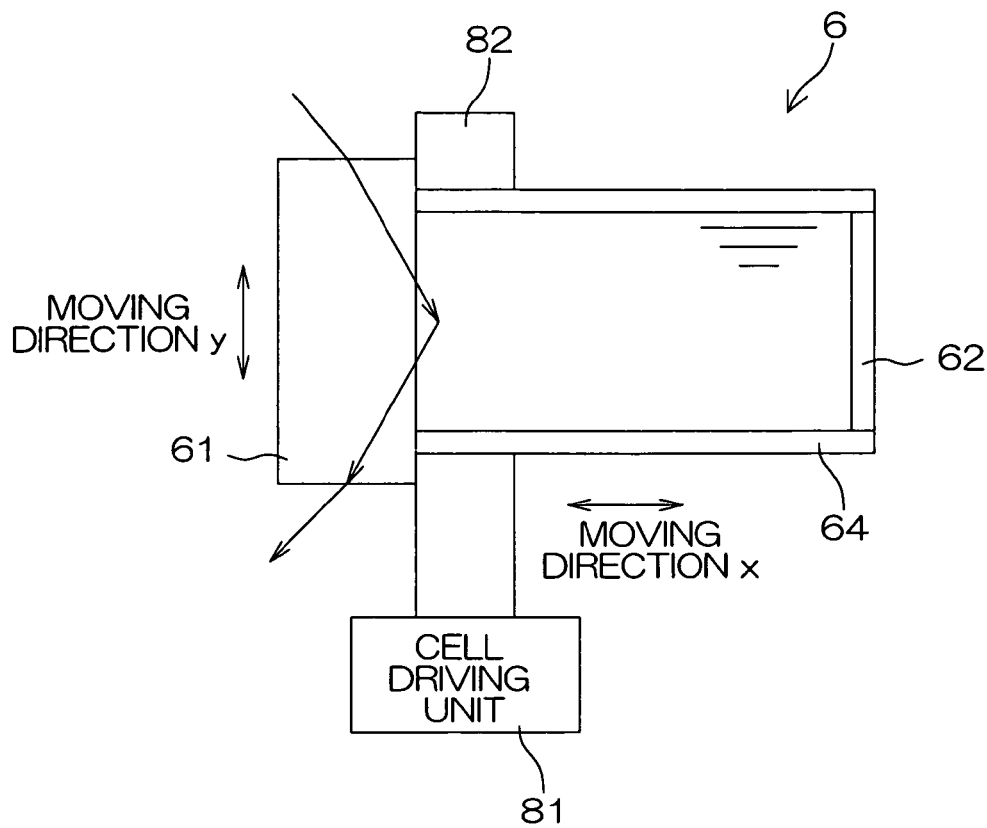
FIG. 4 is a view illustrating an arrangement in which the cell 6 is movable in the x- and y-directions.

As shown in FIG. 4, the cell 6 is fixed to a cell holder 82. The cell holder 82 is connected to a motor-incorporating cell driving unit 81, which enables the cell holder 82 to be movable in the x- and y-directions. Accordingly, the cell 6 is freely movable in the x- and y-directions. By controlling the movement of the cell driving unit 81 in the x- and y-directions, it is possible to optionally set the distance, from the electrode, of the scattering volume portion of the sample S at which the incident light intersects the outgoing light, and it is also possible to optionally set the distance of the scattering volume portion from a wall 64 at the cell lateral side.

Figure 1:
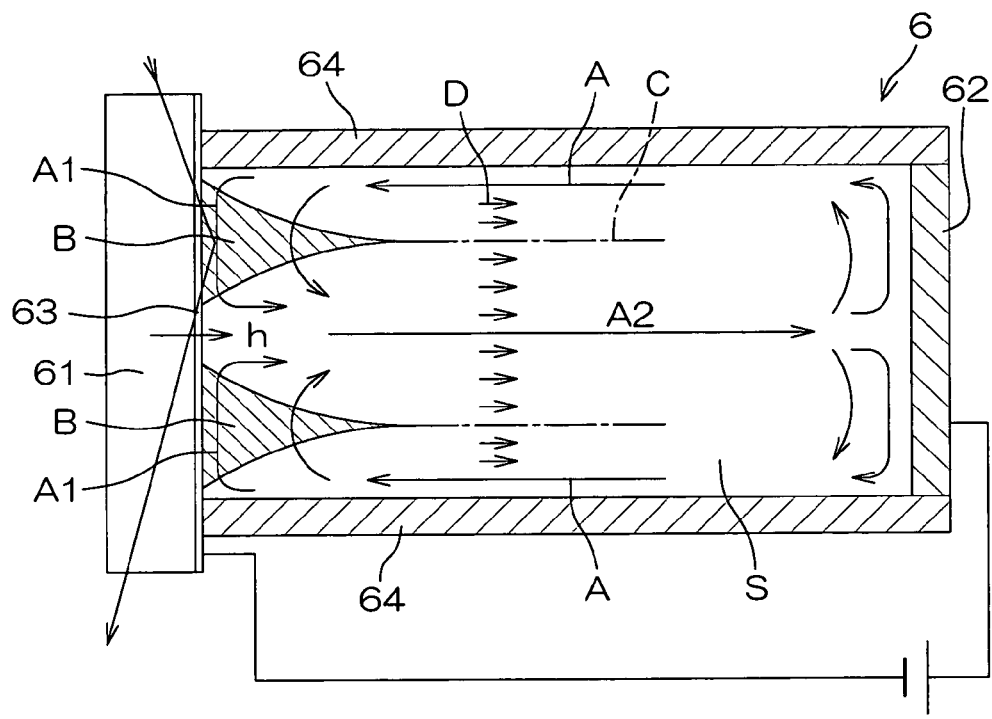
FIG. 1 is a section view of a cell 6 to be used in the present invention.

FIG. 1 is a section view of the cell 6. The cell 6 has a rectangular parallelepiped or cylindrical inside. One of the parallel end sides of the cell 6 is made of transparent quartz glass 61, and the other is formed by a platinum electrode 62. The quartz glass 61 is provided at the inside face thereof with a transparent electrode 63. The lateral wall 64 may be made of an optional material such as glass, ceramic, resin or the like. Unlike in the prior art, the lateral wall 64 is not necessarily required to have optical transparency. Accordingly, it is not important whether the material is transparent or opaque. This increases the degree of freedom for material selection. For example, when there is selected a material excellent in water-shedding quality such as Teflon, the adhesion of the sample can be reduced. Thus, the contamination of the lateral wall 64 can be removed by a simple cleaning. Further, when there is selected a dark-color material less in reflection, this reduces the generation of stray light in the cell, thus assuring a more accurate measurement.

Figure 2:
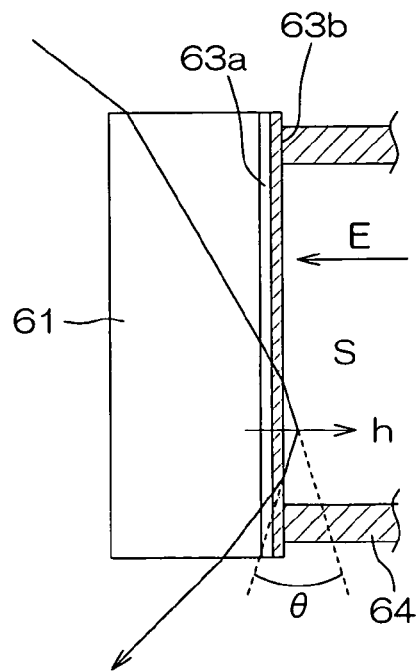
FIG. 2 is an enlarged view of a quartz glass 61 and a transparent electrode 63 forming parts of the cell 6.

FIG. 2 is an enlarged view of the quartz glass 61 and the transparent electrode 63. The quartz glass 61 is coated with an Indium Tin Oxide (ITO) film 63a, which is then coated with platinum 63b. An assembly of the ITO film 63a and the platinum 63b is referred to as the transparent electrode 63. The light is incident upon the cell 6 through the mirror 4, the lens 5, the quartz glass 61, and the transparent electrode 63. The outgoing light, which scatters from the sample S at a predetermined angle θ with respect to the incident angle, outgoes through the transparent electrode 63 and the quartz glass 61 and is then received by the light receiving unit 11 through the pinholes 9 and the lens 10.

As understood from FIG. 2, the laser light incident upon the cell enters the cell through a lateral side of the quartz glass 61. If the laser light is incident upon the cell through the bottom of the quartz glass 61, the light ends up with total reflection at the interface between the quartz glass 61 and the sample solution when it is intended to set a small scattering angle θ. Accordingly, the measurement can be made only at a large scattering angle θ. However, if the scattering angle θ becomes large, the spread of frequency due to particles diffusion is widely observed. This exerts a bad influence to the measurement precision of Doppler displacement. It is therefore preferred to conduct a measurement at a small scattering angle θ. This is why the laser light to be incident upon the cell, is entered into the cell through the lateral side of the quartz glass 61 as shown in FIG. 2.

Figure 5:
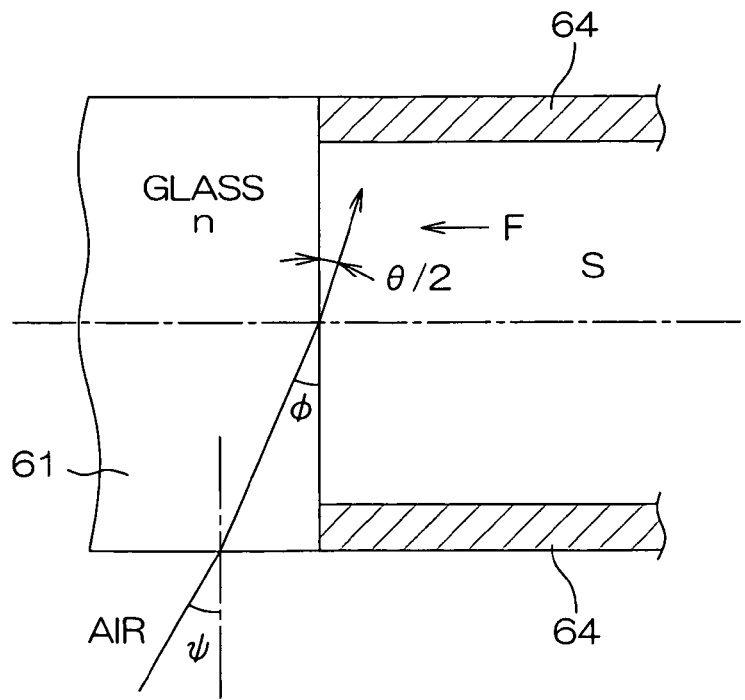
FIG. 5 is a view illustrating the incident light path when laser light is incident upon the cell through a lateral side of the quartz glass 61.

FIG. 5 is a view illustrating an incident light path at the time when laser light is incident upon the cell through the lateral side of the quartz glass 61. In FIG. 5, the incident angle of the laser light with respect to the lateral side of the quartz glass 61, is expressed by φ, the contact angle of the laser light with respect to that face of the quartz glass 61 which comes in contact with the sample S, is expressed by ϕ, and the contact angle of the light entering the sample S from the quartz glass 61, is expressed by θ/2.

It is supposed that the refractive index n of the glass is 1.4564, and that the sample S is water of which refractive index is 1. To set the scattering angle θ to 20°, φ may be set to 25.84° and ϕ may be set to 39.40° according to the calculation using the Snell's law.

Thus, by arranging such that the laser light is incident upon the cell through the lateral side of the quartz glass 61, a small scattering angle θ can be obtained, thus assuring an accurate measurement high in resolution. The use of other glass than quartz produces basically the same effect.

Figure 6:
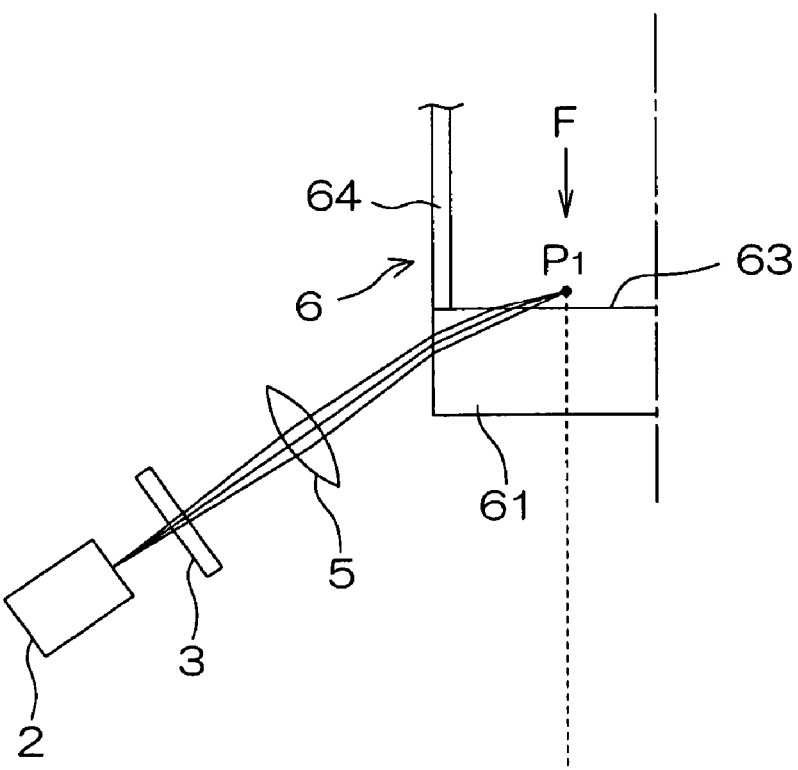
FIG. 6(a) is a side view illustrating an arrangement in which laser light of a laser oscillator 2 is incident upon a lateral side of the quartz glass 61 through an ND filter 3 and a lens 5.
FIG. 6(b) is a plan view of FIG. 6(a).
Figure 6:
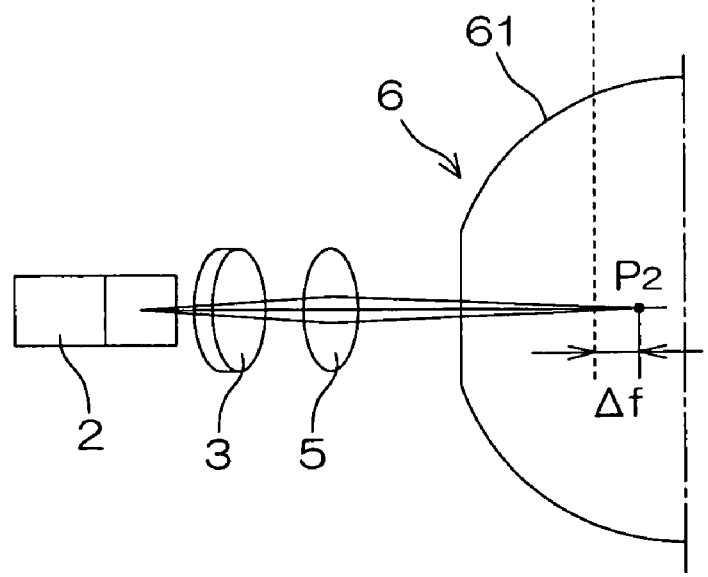

The laser light is obliquely incident upon the quartz glass 61. Accordingly, as to the focal point of the laser light having passed through the lens 5, the focal distance when viewed in the F direction in FIG. 5, is longer than that when viewed in the vertical direction with respect to the paper plane of FIG. 5. FIG. 6(a) is a side view illustrating an arrangement in which laser light of the laser oscillator 2 is incident upon the lateral side of the quartz glass 61 through the ND filter 3 and the lens 5. FIG. 6(b) is a plan view of FIG. 6(a). The focal position P1 in FIG. 6(a) is shorter than the focal position P2 in FIG. 6(b), and the difference is expressed by Δf.

Figure 7:
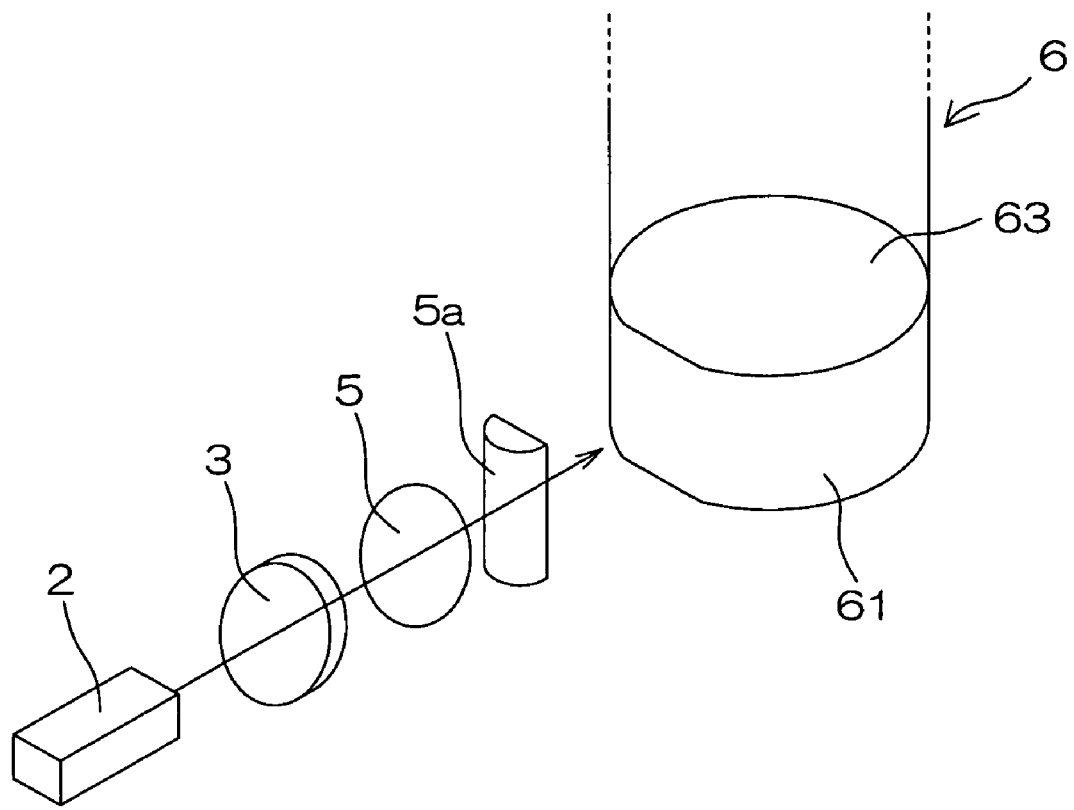
FIG. 7 is a perspective view illustrating an arrangement in which a cylindrical lens 5a is used in the optical path in which laser light is incident upon a lateral side of the quartz glass 61.

To accord these two focal points with each other to obtain Δf=0, a cylindrical lens may be added to the lens 5. FIG. 7 is a view illustrating an arrangement in which a cylindrical lens 5a is added in the optical path in which laser light is incident upon the cell through the lateral side of the quartz glass 61. Although not shown in FIG. 7, a cylindrical lens is also disposed in the optical path in which the light outgoes from the cell through the lateral side of the quartz glass 61. According to the arrangement above-mentioned, the two focal points are accorded with each other to eliminate an image distortion, enabling the scattering volume to be reduced. This minimizes the influence of multiple scattering in a thick sample S, thus increasing the measuring precision.

When the scattering volume can be reduced, the measuring point of the sample S can be brought as close as possible to the electrode face by the operation of the cell driving unit 81. Accordingly, the optical path length in the sample S can be minimized. This advantageously reduces the optical attenuation particularly in a thick sample S.

In the electrophoretic mobility measuring apparatus 1 discussed in the foregoing, the light receiving unit 11 detects the frequency change Δν=ν'−ν'' between the scattering light and the reference light when the electric field was applied to the sample, and then measures, based on this frequency change, the speed of the particles in the direction of the electric field E. Here, the Doppler displacement Δν is expressed by the following formula:

$$\Delta\nu = (\nu q/2\pi)\cos(\theta/2) = (\nu n/\lambda)\sin\theta$$

wherein ν is the particle velocity, q is the magnitude of the scattering vector, n is the refractive index of the sample medium, and λ is the wavelength of the light in the medium.

Here, n, λ, θ are known. Accordingly, when the Doppler displacement Δν is measured, the particle velocity ν can be obtained.

The following description will discuss modifications of the quartz glass and the electrode disposed at the side of the cell 6.

Figure 8:
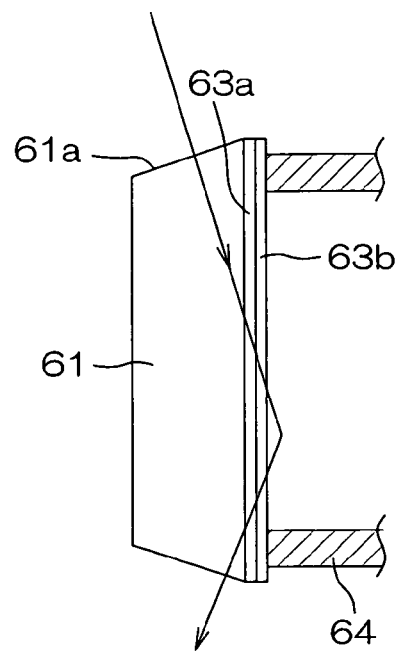
FIG. 8 is a section view illustrating an arrangement in which a light incident face 61a of the quartz glass 61 is obliquely cut.

FIG. 8 is a section view illustrating an arrangement in which a lateral face or light incident face 61a of the quartz glass 61 is obliquely cut. According to this arrangement, the angle formed by the incident light and the upper end face of the quartz glass 61, is made 90 degrees, and the angle formed by the outgoing light and the lower end face of the quartz glass 61, is also made 90 degrees. This reduces the amount of reflection at the time when the incident light is incident upon the quartz glass 61, and also reduces the amount of internal reflection at the time when the scattering light outgoes from the inside of the quartz glass 61.

Figure 9:
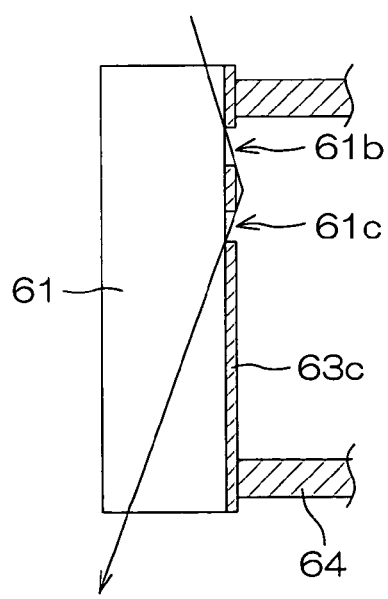
FIG. 9(a) is a section view in side elevation illustrating an example in which a platinum film 63c is thickly formed on the sample-side face of the quartz glass 61 such that this sample-side face becomes opaque.
FIG. 9(b) is a front view of FIG. 9(a)
Figure 9:
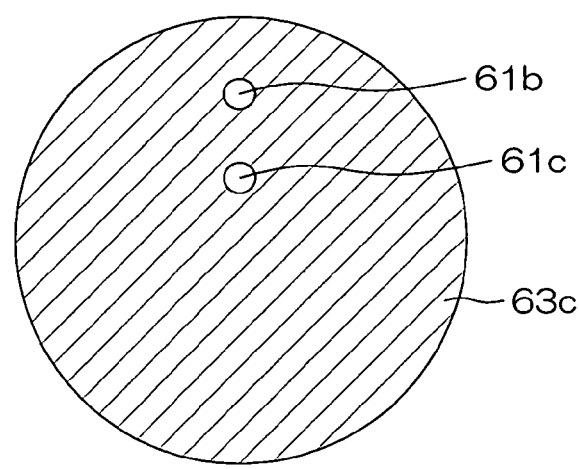

FIG. 9(a) is a section view in side elevation illustrating an example in which a platinum film 63c is thickly formed on the sample-side face of the quartz glass 61 such that this sample-side face becomes opaque. FIG. 9(b) is a front view of FIG. 9(a). The platinum film 63c does not have a light transmitting function, and serves as an electrode. The platinum film 63c is not formed on the quartz glass 61 at at least two portions, i.e., the portion through which the incident light passes, and the portion through which the scattering light passes. At these two portions, the quartz glass 61 is exposed. The quartz-glass exposed portion through which the incident light passes, is referred to as an incident window 61b, and the quartz-glass exposed portion through which the scattering light passes, is referred to as an outgoing window 61c. According to the arrangement above-mentioned, even though no ITO film is disposed, the velocity of the particles in the cell can be measured according to the Doppler method through the incident window 61b and the outgoing window 61c. Since the platinum film 63c can be thickly formed, the electrode electric resistance can readily be reduced.

Figure 10:
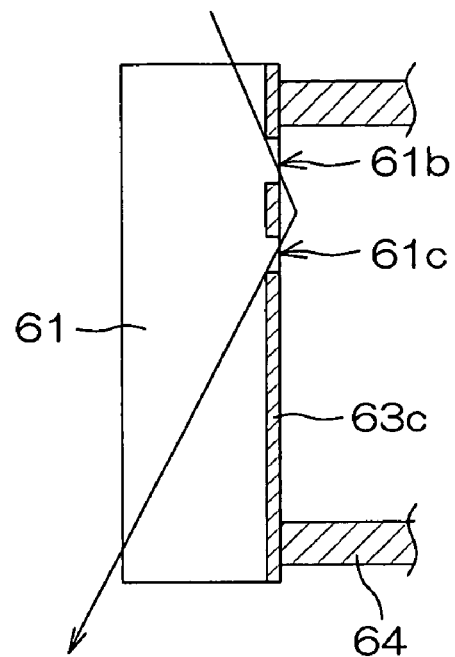
FIG. 10 is a section view illustrating an arrangement in which the sample-side face of the quartz glass 61 is scraped off by a predetermined thickness except for the part upon which incident light is incident and for the part through which scattering light outgoes, and in which a platinum film 63c is formed on the scraped part.
Figure 11:
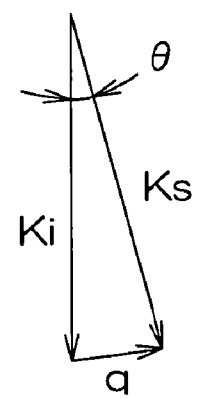
FIG. 11 is a view illustrating a relationship between incident vector ki and outgoing vector ks.

FIG. 10 is a section view illustrating an arrangement in which the sample-side face of the quartz glass 61 is scraped off by a predetermined thickness except for the part through which incident light enters and for the part through which scattering light outgoes, and in which a platinum film 63c is formed on the scraped part. In this arrangement, too, the incident light enters as passing through an incident window 61b to which the quartz glass 61 is exposed, and the scattering light outgoes as passing through an outgoing window 61c, likewise in FIG. 9. The platinum film 63c does not have a light transmitting function, and serves as an electrode.

The foregoing has discussed embodiments of the present invention. However, the present invention should not be construed as limited to these embodiments, but various modifications can be made within the scope of the present invention.

EXAMPLES

Figure 12:
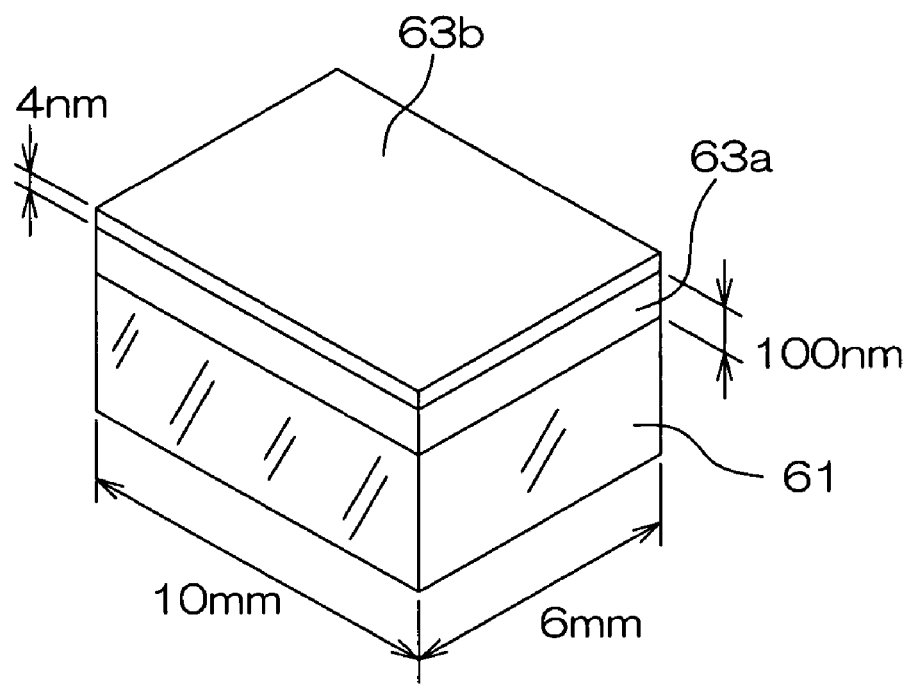
FIG. 12 is a perspective view of an arrangement in which an ITO film 63a serving as a transparent electrode is formed on the quartz glass 61, and is then coated with a platinum 63b.
Figure 13:
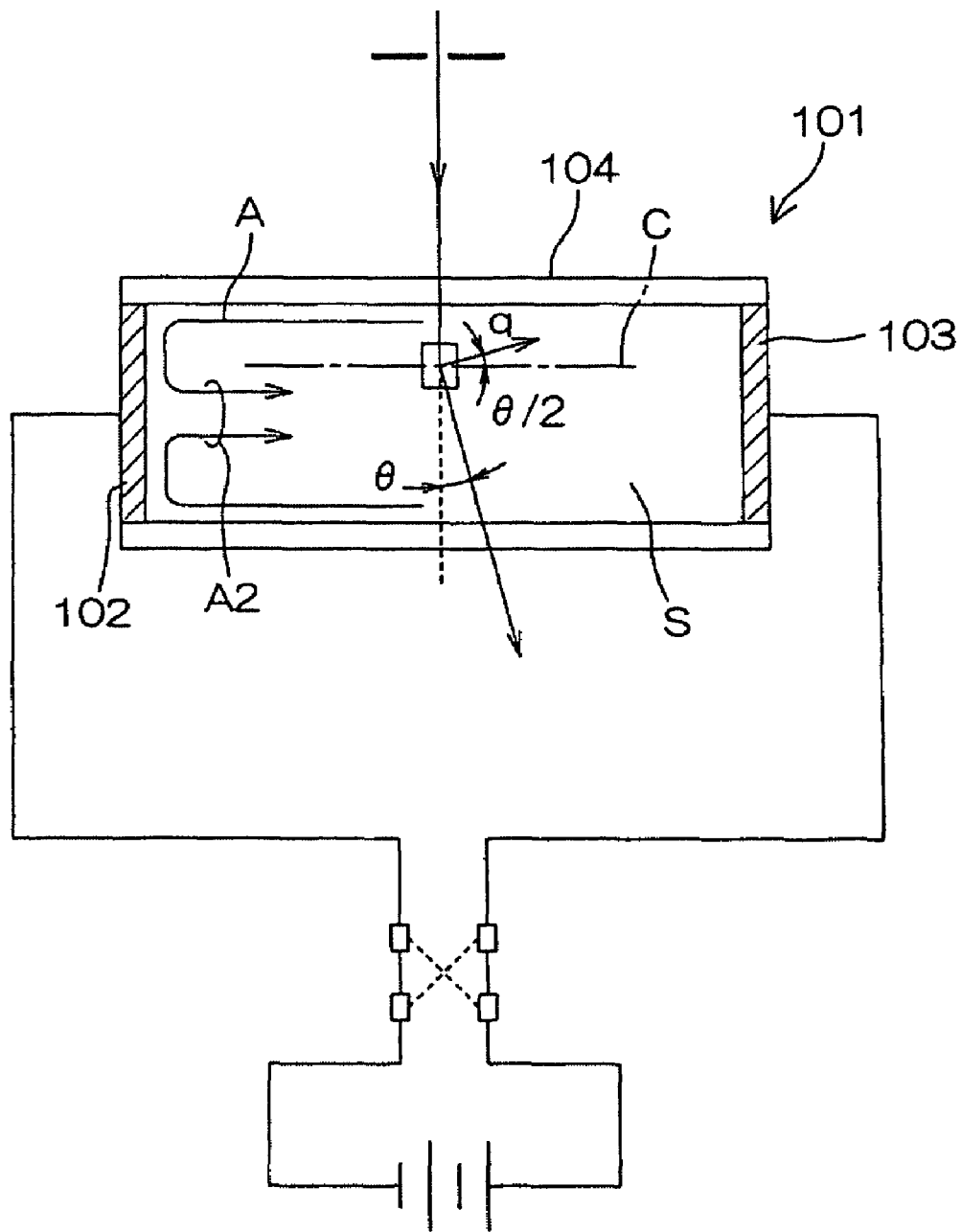
FIG. 13 is a schematic section view of a conventional electrophoretic mobility measuring apparatus.

As shown in FIG. 12, an ITO film 63a having a width of 10 mm, a thickness of 100 nm and a length of 6 mm was formed on a quartz glass 61, and then coated with a platinum 63b having a thickness of about 4 nm. The light transmission in the vertical direction was measured as about 50%. The electric resistance value between the end faces was calculated. That is, the ITO's resistance value was 8.4Ω since the ITO's electric resistivity was $1.4 \times 10^{-4}$ Ωcm and the end-face section area was $10^{-5}$ cm². The platinum's electric resistivity is $10 \times 10^{-6}$ Ωcm. However, the electric resistivity of platinum in the form of a thin film, seems to be a half of the value above-mentioned. Since the end-face section area was $4 \times 10^{-7}$ cm², the platinum's electric resistivity was 38.25Ω. The combined resistance was equal to 1/(1/8.4+1/38.25)=6.9Ω. Accordingly, since the platinum film is thin even though the platinum's electric resistivity itself is low, the use of platinum does not contribute so much to reduction in electric resistivity.

An ITO film 63a having a thickness of 100 nm was formed on the quartz glass 61 of the cell 6 shown in FIG. 1, and a platinum 63b having a thickness of about 4 nm was formed on the ITO film 63a. Two types of water solutions of 10 m mols of NaCl and 100 m mols of NaCl were put inside of the cell 6. Then, a voltage of 300V was applied to the transparent electrode 63 as switched per second. Even after the passage of 50 hours, no change was observed in light transmission and electric resistance. It is therefore considered that the platinum film served well as a protective film.

What we claim is:

1. An electrophoretic mobility measuring apparatus comprising:
    a cell capable of being filled with a sample, the cell including at least one cell wall;
    a transparent electrode forming a part of the at least one cell wall;
    an other electrode opposite to the transparent electrode;
    a voltage applying means for applying a voltage across both electrodes;
    a light incident unit for entering light into a region of the cell, wherein an electroosmotic flow substantially parallel to a face of the transparent electrode is generated through the transparent electrode;
    a light receiving unit for receiving, through the transparent electrode, outgoing light which scatters from the sample in the cell at a predetermined angle θ with respect to the incident angle; and
    a measuring unit for measuring the Doppler displacement of particles in the sample based on the difference in frequency between the incident light and the outgoing light, a direction of a scattering vector which is the vector difference between incident and outgoing vectors, being substantially identical with that of the normal line of the transparent electrode face.

2. An electrophoretic mobility measuring apparatus according to claim 1 wherein the direction of the scattering vector is substantially identical with that of an electric field.

3. An electrophoretic mobility measuring apparatus according to claim 1 wherein the cell-side face of the transparent electrode is coated with platinum or a platinum alloy.

4. An electrophoretic mobility measuring apparatus according to claim 1 wherein the cell inside is a casing-shape body provided at both end faces thereof with the electrodes, one of which is the transparent electrode.

5. An electrophoretic mobility measuring apparatus according to claim 4 wherein a scattering light measuring point is located between the center line of a rectangular parallelepiped or cylindrical casing-shape body, and an inner wall of a lateral side thereof.

6. An electrophoretic mobility measuring apparatus according to claim 1, further comprising cell driving means for moving the cell in the direction of a normal line of the transparent electrode face, and in the direction at right angles to the normal line direction.

7. An electrophoretic mobility measuring apparatus according to claim 1 wherein the light incident unit uses a cylindrical lens for focusing the light on a scattering volume portion.

8. An electrophoretic mobility measuring apparatus according to claim 1 wherein the light receiving unit uses a cylindrical lens for detecting the light from a scattering volume portion.

9. An electrophoretic mobility measuring apparatus comprising:
    a cell capable of being filled with a sample, the cell including at least one cell wall;
    an opaque electrode forming a part of the at least one cell wall, wherein the opaque electrode has a transparent incident window upon which incident light is incident, and a transparent outgoing window through which outgoing light outgoes;
    an other electrode opposite to the opaque electrode;
    a voltage applying means for applying a voltage across both electrodes;
    a light incident unit for entering light into a region of the cell, wherein an electroosmotic flow substantially parallel to a face of the opaque electrode is generated through the transparent incident window of the opaque electrode;
    a light receiving unit for receiving the outgoing light which scatters from the sample in the cell at a predetermined angle θ with respect to the incident angle through the transparent outgoing window of the opaque electrode; and
    a measuring unit for measuring the Doppler displacement of particles in the sample based on the difference in frequency between the incident light and the outgoing light, a direction of a scattering vector which is the vector difference between incident and outgoing vectors, being substantially identical with that of the normal line of the opaque electrode face.

10. An electrophoretic mobility measuring apparatus according to claim 9 wherein the direction of the scattering vector is substantially identical with that of an electric field.

11. An electrophoretic mobility measuring apparatus according to claim 9 wherein a cell-side face of the opaque electrode is coated with platinum or a platinum alloy.

12. An electrophoretic mobility measuring apparatus according to claim 9 wherein the opaque electrode is formed on a transparent substrate, the light incident unit is arranged to enter light through one lateral side of the transparent substrate, and the light receiving unit is arranged to receive the light which outgoes through an other lateral side of the transparent substrate.

13. An electrophoretic mobility measuring apparatus according to claim 9, further comprising cell driving means for moving the cell in the direction of a normal line of the opaque electrode face, and in the direction at right angles to a normal line direction.

14. An electrophoretic mobility measuring apparatus according to claim 9 wherein the light incident unit uses a cylindrical lens for focusing the light on a scattering volume portion.

15. An electrophoretic mobility measuring apparatus according to claim 9, wherein the light receiving unit uses a cylindrical lens for detecting the light from a scattering volume portion.

16. An electrophoretic mobility measuring apparatus comprising:
    a cell capable of being filled with a sample, the cell including at least one cell wall;
    a transparent electrode forming a part of the at least one cell wall;
    an other electrode opposite to the transparent electrode;

a voltage applying means for applying a voltage across both electrodes;

a light incident unit for entering light into the cell through the transparent electrode;

a light receiving unit for receiving, through the transparent electrode, outgoing light which scatters from the sample in the cell at a predetermined angle θ with respect to the incident angle; and a measuring unit for measuring the Doppler displacement of particles in the sample based on the difference in frequency between the incident light and the outgoing light, a direction of a scattering vector which is the vector difference between incident and outgoing vectors, being substantially identical with that of the normal line of the transparent electrode face, wherein the transparent electrode is formed on a transparent substrate that has at least two lateral sides besides a face on which the transparent electrode is formed, and the light incident unit is arranged to enter light through one lateral side of the transparent substrate, and the light receiving unit is arranged to receive the light which outgoes through an other lateral side of the transparent substrate.

17. An electrophoretic mobility measuring apparatus according to claim 16, wherein the direction of the scattering vector is substantially identical with that of an electric field.

18. An electrophoretic mobility measuring apparatus according to claim 16, wherein the cell-side face of the transparent electrode is coated with platinum or a platinum alloy.

19. An electrophoretic mobility measuring apparatus according to claim 16, wherein the cell inside is a casing-shape body provided at both end faces thereof with the electrodes, one of which is the transparent electrode.

20. An electrophoretic mobility measuring apparatus according to claim 19, wherein a scattering light measuring point is located between the center line of a rectangular parallelepiped or cylindrical casing-shape body, and an inner wall of a lateral side thereof.

21. An electrophoretic mobility measuring apparatus according to claim 16, further comprising cell driving means for moving the cell in the direction of a normal line of the transparent electrode face, and in the direction at right angles to the normal line direction.

22. An electrophoretic mobility measuring apparatus according to claim 16, wherein the light incident unit uses a cylindrical lens for focusing the light on a scattering volume portion.

23. An electrophoretic mobility measuring apparatus according to claim 16, wherein the light receiving unit uses a cylindrical lens for detecting the light from a scattering volume portion.

* * * * *